United States Patent [19]

Orlowski et al.

[11] Patent Number: 4,495,172

[45] Date of Patent: Jan. 22, 1985

[54] NAIL COATING

[75] Inventors: Jan A. Orlowski, Altadena; David V. Butler, West Covina; Patrick D. Kidd, Sierra Madre, all of Calif.

[73] Assignee: Scientific Pharmaceuticals, Inc., Duarte, Calif.

[21] Appl. No.: 118,303

[22] Filed: Feb. 4, 1980

[51] Int. Cl.$^3$ ............................................. A61K 7/043
[52] U.S. Cl. ................................................ 424/61
[58] Field of Search ........................................ 424/61

[56] References Cited

U.S. PATENT DOCUMENTS

| | | | |
|---|---|---|---|
| 2,073,867 | 3/1937 | Feingenbaum | 132/73 |
| 2,633,139 | 3/1953 | Pettey | 132/73 |
| 2,688,331 | 9/1954 | Bogolowsky | 132/73 |
| 2,941,535 | 6/1960 | Lappe | 132/73 |
| 2,979,061 | 4/1961 | Greenman et al. | 132/73 |
| 3,037,514 | 6/1962 | Lappe | 132/88.7 X |
| 3,157,912 | 11/1964 | Lisczawaka | 18/5.1 |
| 3,425,426 | 2/1969 | Welanetz | 132/73 |
| 3,478,756 | 11/1969 | Sautter et al. | 132/73 |
| 3,483,289 | 12/1969 | Michaelson et al. | 132/73 X |
| 3,487,831 | 1/1970 | Jaume et al. | 132/73 X |
| 3,502,088 | 3/1970 | Jarby | 132/73 |
| 3,552,401 | 1/1971 | Michaelson et al. | 132/73 |
| 3,574,822 | 4/1971 | Shepherd | 424/61 |
| 3,645,835 | 2/1972 | Hodgson | 428/195 |
| 4,058,442 | 11/1977 | Lee, Jr. et al. | 424/61 |
| 4,104,333 | 8/1978 | Lee, Jr. et al. | 424/61 |

OTHER PUBLICATIONS

John Wiley & Sons, 1964, Encyclopedia of Polymer Science, vol. I, pp. 263–297.

*Primary Examiner*—Dale R. Ore
*Attorney, Agent, or Firm*—Cushman, Darby & Cushman

[57] ABSTRACT

A composition, method and product are provided for the coating of human nails. The coating composition comprises a curable ethoxyethylmethacrylate monomer, a polyethylmethacrylate homopolymer or copolymer filler and a cross-linking agent. The method involves applying the coating composition upon nails and curing the composition. The product involves a separately packaged liquid and powder, wherein the liquid comprises ethoxyethylmethacrylate monomer and a cross-linking agent and the powder comprises a polyethylmethacrylate filler.

17 Claims, No Drawings

NAIL COATING

BACKGROUND OF THE INVENTION

The present invention relates to a composition, method and product for coating human nails.

A variety of methods for beautifying and strengthening human nails are known. One such method involves the attachment of preformed artificial nails to human nails. Examples of such techniques are illustrated in the following U.S. Pat. Nos. 2,633,139 (Pettey); 2,688,331 (Bogoslowsky); 2,941,535 (Lappe); 2,979,061 (Greenman et al.); 3,487,831 (Jaume et al.); 3,502,088 (Jarby); 3,552,401 (Michaelson et al.); and 3,645,835 (Hodgson).

More particularly, the Lappe U.S. Pat. No. 2,941,535 describes a preformed artificial nail which is affixed to the surface of a natural nail by means of an adhesive. The adhesive may comprise a polymerizable acrylic ester monomer, such as ethylmethacrylate, methylmethacrylate, butylmethacrylate and the like, which preferably has a polymeric filler dissolved therein. According to this patent, the preformed artificial nail is provided with holes to permit the adhesive to form an interconnecting bond between an overcoat and an undercoat of the artificial nail, thereby more firmly affixing the artificial nail to the surface of the natural nail.

The Hodgson U.S. Pat. No. 3,645,835 describes a cast film consisting of a copolymer of 80% by volume ethoxyethylmethacrylate (EEMA) and 20% by volume hydroxyethylmethacrylate (HEMA) onto which is spread a solvent-based polyvinyl ethyl ether pressure-sensitive adhesive (note Example 6 at column 11, lines 35–50). The cast film may then be attached to a human nail by means of the pressure-sensitive adhesive.

Another technique for the treatment of nails is described in the Welanetz U.S. Pat. No. 3,425,426, whereby split or broken nails are repaired by means of a shear fabric patch. This technique is similar to the above-mentioned application of a preformed artificial nail to human nails in that both techniques involve the attachment of a solid, preformed lamina to the surface of a nail. On the other hand, these techniques are distinguishable from techniques involving the application of a curable or hardenable liquid substance to a nail, whereby this curable substance hardens on the surface of the nail in the absence of an attached, solid, preformed lamina. An example of the latter technique is provided in the Michaelson et al. U.S. Pat. No. 3,483,289. In this Michaelson et al. patent there is described a human nail coating comprising a plasticizer, an albuminoid, an organic solvent and one or more of a cellulosic derivative, a natural resin or a synthetic resin. When applied to a nail, this coating hardens primarily by solvent evaporation (See column 1, lines 61–65). Such hardened coatings permit broken or split nails to mend and to elongate by natural growth without further breaking or splitting.

The Shepherd et al. U.S. Pat. No. 3,574,822 describes the incorporation of cross-linkable hydrophilic hydroxy lower alkyl acrylates and methacrylates into cosmetic compositions. Shepherd et al. indicate that these compositions may be applied to the hair or skin, as well as to human nails.

In addition to mending and strengthening nails, a hardenable substance may be applied to the surface of nails to give the appearance of lengthened or elongated nails. According to such techniques, a hardenable substance may be supported over the end of a nail by means of a removable support. For example, the Feingenbaum U.S. Pat. No. 2,073,867 and the Sautter et al. U.S. Pat. No. 3,478,756 describe removable supports which are placed underneath the tips of the nail, whereas the Lappe U.S. Pat. No. 3,037,514 and the Lisczawaka U.S. Pat. No. 3,157,912 describe removeable molds which are placed over the upper surface of the nail. After the hardenable substance cures, the support is removed and the hardened coating may be filed to conform to the shape of an elongated nail.

Perhaps the most widely used products for mending and elongating natural nails are methacrylate resin based formulations, e.g., note the disclosures of U.S. Pat. Nos. 3,037,514 (Lappe); 3,157,912 (Lisczawka); and 3,478,756 (Sautter et al.). These formulations may consist of two parts that after mixing have a suitable consistency to make easy to shape coatings, hardening to form a nail-like material.

Chronologically, one of the first and probably still the most commonly known and marketed formulations comprise a liquid being principally a methylmethacrylate or lower alkyl methacrylate monomer and a powder being polymethylmethacrylate. The liquid part contains a polymerization accelerator and the powder a polymerization initiator. When mixed together, the accelerator and initiator trigger the free radical initiated polymerization of methacrylate resins causing the material to cure. In order to achieve a smooth, easy flowing and easy to shape mix, the powder should dissolve, at least in part, in the liquid prior to cure. Different additives are incorporated in the formulations contributing to improved esthetics, color stability, shelf-life and other characteristics of the material.

Unfortunately however, the formulations based on methylmethacrylate (or poly lower alkyl methacrylate)/polymethylmethacrylate resins have very serious inherent drawbacks and disadvantages. Methylmethacrylate is a known skin irritant and sensitizer. It possesses a strong and unpleasant odor and its vapors are toxic and irritating to the eyes. Ethyl, propyl, isopropyl and other lower alkyl methacryalates also have, although usually to a lower degree, the same negative characteristics as those of methyl methacrylate (being at the same time inferior as a solvent for polymethylmethacrylate and therefore, contributing to worse handling properties and poor esthetics of the material). Also methyl methacrylate based artificial fingernails have markedly better mechanical properties than those made of its homologues, especially with respect to flexural strength and brittleness. Another disadvantage of formulations based on methyl methacrylate and its homologues is a high exotherm during curing causing considerable discomfort to the person involved.

Several nail mender and lengthener formulations based on methacrylate resins other than lower alkyl methacrylates have been or are in use or described in the literature. For example, the Lee, Jr., et al. U.S. Pat. No. 4,058,442 and the Lee, Jr., et al. U.S. Pat. No. 4,104,333 describe formulations based primarily on tetrahydrofurfuryl methacrylate and aliphatic di- or polymethacrylates. These formulations, however, although apparently biologically less harmful than those based on lower alkylmethacrylates, also had serious drawbacks that were found very objectionable to users. In general, they were more difficult to apply than methyl methacrylate based formulations due to poor solubility of polymeric powder in the liquid part. After cure, the surface had a thick layer of partially cured material that made finishing difficult and time consuming. The cured material was brittle and once a crack formed, it propagated easily. The use of special plasticizing additives became a must in these formulations and while they were to some degree beneficial in improving flexibility and crack resistance of the cured material, their presence was undesirable from the point of view of ease of application and finishing and in some cases because of esthetics of the cured material.

Accordingly, there is a need in the art for compositions, methods and products for coating human nails.

SUMMARY OF THE INVENTION

Therefore, it is an object of the present invention to provide a human nail coating composition including the following components:
(i) from about 21% to about 53% by weight of ethoxyethylmethacrylate;
(ii) from about 0.2% to about 11% by weight of a cross-linking agent having at least two methacrylate groups per molecule; and
(iii) from about 45% to about 71% by weight of a polymeric filler having at least 70% of ethylmethacrylate groups in a homopolymer or a copolymer;
whereby these components, when mixed, have a consistency sufficient to permit application to human nails, and whereby this composition is capable of curing within about 60 seconds to about 360 seconds upon application to human nails.

It is another object of the invention to provide a method for coating human nails including the steps of:
(a) applying a curable liquid to human nails, said liquid comprising from about 21% to about 53% by weight of ethoxyethylmethacrylate, from about 0.2% to about 11% by weight of a cross-linking agent having a least two methacrylate groups per molecule, and from about 45% to about 71% by weight of a polymeric filler having at least 70% of ethylmethacrylate groups in a homopolymer or a copolymer; and
(b) curing said curable liquid applied to said nails within about 60 seconds to about 360 seconds.

It is still another object of the invention to provide a two-package human nail coating product including:
(A) a liquid comprising from about 75% to about 97% by weight of ethoxyethylmethacrylate, and from about 1% to about 20% by weight of a cross-linking agent having at least two methacrylate groups per molecule; and
(B) a powder comprising a polymeric filler having at least 70% of ethylmethacrylate groups in a homopolymer or a copolymer,
wherein the liquid (A) and the powder (B) are separately contained in the coating product.

DETAILED DESCRIPTION OF THE INVENTION

The present invention relates to a composition, method and product for the brush-on-type application of a mending, strengthening and/or elongating coating to nails.

Brush-on-type nail coating compositions should have the dual property of having a sufficient consistency to permit proper application to nails, while at the same time having the ability to harden or cure upon application to nails without discomfort and within a relatively short period of time. Accordingly, it is necessary to carefully select particular nail coating components in proper quantitites in order to achieve this desired dual property.

According to the present invention, a nail coating composition, which has a consistency sufficient to permit application to human nails and which is capable of curing within about 60 seconds to about 360 seconds upon application, can be achieved by combining in admixture sufficient quantitites of an ethoxyethylmethacrylate monomer, a cross-linking agent having at least two methacrylate groups per molecule and a polymeric filler having at least 70% of ethylmethacrylate groups in a homopolymer or a copolymer. More particularly, this coating composition contains from about 21% to about 53% by weight of ethoxyethylmethacrylate, from about 0.2% to about 11% by weight of the cross-linking agent, and from about 45% to about 71% by weight of the polymeric filler.

As pointed out in the *Encyclopedia of Polymer Science and Technology*, John Wiley and Sons, Inc., volume 1, pp. 263–97 (1964), the disclosure of which is incorporated herein by reference, acrylic and methacrylic esters may be polymerized or cured by a variety of techniques. Obviously, certain of these techniques such as radiation-induced polymerization with gamma rays are not practicable for curing nail coatings. However, it is noted that the Lee, Jr., et al. U.S. Pat. No. 4,058,442, the disclosure of which is also incorporated herein by reference, describes the photopolymerization of a nail coating composition.

For the purposes of the specific nail coating compositions of the present invention, a chemically initiated curing technique is preferred. Thus, in order to induce curing of the nail coating compositions of the present invention, a free-radical catalyst may be incorporated into the coating components. Organic peroxide initiators, such as lauroyl peroxide and especially benzoyl peroxide, are preferred.

The ability of the initiator to cure the nail coating composition may be enhanced through the use of activators or accelerators. Thus, a peroxide initiator can be activated with a tertiary aromatic amine such as an N,N-di(lower)alkyl-p-toluidine (e.g., N,N-dimethyl-p-toluidine, N,N-diethyl-p-toluidine, and especially N,N-bis(2-hydroxyethyl)-p-toluidine).

The various components of the nail coating composition may be combined in any suitable manner. However, since chemically initiated polymerization starts immediately upon admixture of all three of (1) methacrylic monomers, (2) an initiator and (3) an activator, it is necessary to separate at least one of these components from the others until immediately before the application of the nail coating to human nails. This separation may be achieved through the use of a two-package product, wherein various components of the nail coating composition are separately contained until the time of application to nails.

Therefore, according to one embodiment of the present invention, the components of the nail coating composition may be separated by means of a two-package product into two parts, one being in the form of a liquid and the other in the form of a powder. The liquid part comprises at least about 75% but no more than about 97% of ethoxyethylmethacrylate and at least about 1% but no more than about 20% of cross-linking di, tri- or polymethacrylate monomer and polymerization initiator or accelerator. The powder part contains at least about 70% of polyethylmethacrylate in the form of homo- or copolymer and polymerization initiator or accelerator. Either or both parts may contain also other additives such as dyes, pigments, thickening agents, plasticizers, etc.

Although the above-mentioned liquid/powder two-package system is preferred, it will be appreciated that other two-package systems may be employed. For instance, the Lee, Jr., et al. U.S. Pat. No. 4,104,333, the disclosure of which is also incorporated herein by reference, describes a two-package system wherein one "package" contains approximately half of the polymerizable components plus all of the accelerator and the other package contains the remaining half of the polymerizable components plus all of the initiator (note Example IV at column 5, line 63 to column 6, line 20). Furthermore, the Sautter et al. U.S. Pat. No. 3,478,756 describes another two composition curing system (note column 6, line 46 to column 7, line 15). The first composition constitutes a primer or a lacquer containing a film forming resinous material, an oxidizing catalyst and a volatile solvent. The second composition contains a solution or paste of a polymeric film forming material mixed with a resin-forming monomer. The first and second compositions are applied sequentially to the surface of the nail.

Of course, when an appropriate curing system is used, it is possible to include all of the nail coating components in one package without fear of polymerization taking place therein. Nonetheless, whichever system is used, it is helpful to package polymerizable components with a stabilizer such as a butylated hydroxytoluene (BHT), in order to enhance the storage stability of the components.

The amount of accelerators and/or initiators used should be sufficient to achieve the desired properties of storage stability, applicability of the coating to nails, and rate of cure upon application. Therefore, the amount of initiators used is somewhat dependent upon the amount and concentration of polymerizable components present. Nonetheless, ranges of about 0.2% to about 4.0% by weight of a peroxide-type initiator and about 0.1% to about 8% by weight of a tertiary aromatic amine accelerator are most useful.

Preferred cross-linking agents include ethylene-, diethylene, triethylene- and polyethyleneglycol dimethacrylates; propylene-, dipropylene-, tripopylene-, and polypropyleneglycol dimethacrylates; hexandediol dimethacrylates; trimethylolpropane trimethacrylates; 2,2 bis[4'(3"-methacroyl-2'-hydroxypropoxy)phenyl] propane; 2,2 bis[4'(methacroylethoxy)phenyl] propane; 1,4 bis(methacroylmethyl) cyclohexane; and 2,2 bis(4'-methacroylphenyl) propane. Other similar compounds having at least two methacrylate groups per molecule may also be used such as 2,2-bis(2'-methacroylphenyl) propane or 1,4-butylene dimethacrylate.

It has been found that the nail coating compositions of the present invention exhibit superior properties especially with respect to low irritation potential to the skin, good flexibility and crack resistance and ease of finishing due to the insignificance or non-existence of a soft layer on the top of the cured material. Especially the last characteristic was entirely unexpected as an uncured or only partially cured surface layer is a common occurrence with methacrylate resins that are known as being susceptible to oxygen inhibition.

Good working characteristics of the nail coating compositions are a result of an unexpected finding that polyethylmethacrylate or copolymers, e.g., polyethylmethacrylate/polymethymethacrylate copolymers, in which ethylmethacrylate moieties constitute a significant portion of the original monomeric constituents, dissolve at the fast rate in a liquid comprised primarily of ethoxyethylmethacrylate.

When a liquid/powder two-package system is used, the ratio of liquid to powder in a mix may vary from about 1.2 to 1 to about 1 to 2.5 depending on the particular formulation and application technique.

As mentioned previously, the nail coating compositions may contain various additives. For example, in addition to a polyethylmethacrylate filler, other fillers or thickeners may also be used such as inorganic fillers, e.g., finely-divided alumina silicates, silica, quartz, glass and the like. Minor amounts of dyes or pigments (e.g., titanium dioxide) may also be used. Moreover, the nail coating composition may further include plasticizers such as esters of aromatic compounds.

The following examples will further illustrate the invention.

EXAMPLE 1

A nail coating composition was formulated as follows:

| LIQUID | % WEIGHT | POWDER | % WEIGHT |
| --- | --- | --- | --- |
| Ethoxyethyl methacrylate | 95 | Copolymer of polyethyl and polymethylmethacrylate | 98.9 |
| Diethyleneglycol dimethacrylate | 2 | | |
| N,N—bis (2-hydroxyethyl)-p-toluidine | 2.9 | Benzoyl peroxide | 1 |
| | | Titanium dioxide | 0.1 |
| BHT (inhibitor) | 0.1 | | |

This material was mixed at a 1:2 ratio of liquid to powder and was used for coating nails. It cured forming a flexible and non-brittle polymer of most satisfactory properties from the point of view of esthetics. The application was easy because of good compatibility of the liquid with the powder and it required very little finishing because the unpolymerized surface layer was virtually non-existent and because of homogeneity of the cured material.

EXAMPLE 2

A nail coating composition was formulated as follows:

| LIQUID | % WEIGHT | POWDER | % WEIGHT |
| --- | --- | --- | --- |
| Ethoxyethyl methacrylate | 94 | Polyethylmethacrylate | 98.9 |
| 1,6-hexanediol dimethacrylate | 3 | Benzoyl peroxide | 1.0 |
| N,N—bis (2-hydroxyethyl)-p-toluidine | 2.9 | Titanium dioxide | 0.1 |
| BHT | 0.1 | | |

This material was mixed at a 1:2 ratio of liquid to powder and was used for coating nails. It represented, in certain respects, further improvement over the formulation described in Example 1. the homogeneity and esthetics as well as flexibility and crack resistance were very good. Application and finishing characteristics were most satisfactory.

COMPARATIVE EXAMPLE A

A nail coating composition was formuated as follows:

| LIQUID | % WEIGHT | POWDER | % WEIGHT |
|---|---|---|---|
| Ethoxyethylmethacrylate | 50 | Polyethylmethacrylate | 98.9 |
| Triethyleneglycol dimethacrylate | 46.9 | Benzoyl peroxide (initiator) | 1 |
| N,N bis (2-hydroxyethyl)-p-toluidine (activator) | 3 | Titanium dioxide (opacifier) | 0.1 |
| BHT | 0.1 | | |

This material was mixed at a 1:2 ratio of liquid to powder and was used for coating nails. It exhibited a satisfactory curing time of about 200 seconds, but it was difficult to apply due to incompatibility of powder and liquid. When curing, the material was generating an excessive heat and discoloring. The finishing was very difficult because of a thick soft layer of partially cured material left on the surface and because of poor homogeneity of the underlaying layer. The cured product was brittle and esthetically poor.

COMPARATIVE EXAMPLE B

A nail coating composition was formulated as follows:

| LIQUID | % WEIGHT | POWDER | % WEIGHT |
|---|---|---|---|
| Ethoxyethylmethacrylate | 91.9 | Polymethylmethacrylate | 98.9 |
| Triethyleneglycol dimethacrylate | 5 | Benzoyl peroxide | 1 |
| N,N bis (2-hydroxyethyl)-p-toluidine | 3 | Titanium dioxide | 0.1 |
| BHT | 0.1 | | |

This material was mixed at a 1:2 ratio of liquid to powder and was used for coating nails. It represented a significant improvement over the material described in comparative Example A. There was only a moderate exotherm generated during curing and virtually no discoloration was observed. The uncured layer was greatly reduced. The application was, however, uneasy due to poor solubility of the powder in the liquid and the cured material had a tendency to crack. Its homogeneity was poor, affecting esthetics and requiring more polishing time.

While certain representative embodiments and details have been shown for the purpose of illustrating the invention, it will be apparent to those skilled in the art that various changes and modifications may be made therein without departing from the spirit or scope of the invention. It will further be understood that the invention may comprise, consist essentially of or consist of the steps or materials recited herein.

What is claimed is:

1. A human nail coating composition comprising the following components:
   (i) from about 21% to about 53% by weight of ethoxyethylmethacrylate;
   (ii) from about 0.2% to about 11% by weight of a cross-linking agent having at least two methacrylate groups per molecule; and
   (iii) from about 45% to about 71% by weight of a polymeric filler having at least 70% of ethylmethacrylate groups in a homopolymer or a copolymer with methyl methacrylate,
   whereby said components, when mixed, have a consistency sufficient to permit application to human nails, and whereby said composition is capable of curing within about 60 seconds to about 360 seconds upon application to human nails.

2. A composition according to claim 1, wherein said cross-linking agent is selected from the group consisting of ethylene-, diethylene-, triethylene- and polyethyleneglycol dimethacrylate; propylene-, dipropylene-, tripropylene-, and polypropyleneglycol dimethacrylate; hexanediol dimethacrylate; trimethylolpropane trimethacrylate; 2,2 bis[4'(3"-methacroyl-2'-hydroxypropoxy)phenyl] propane; 2,2 bis[4'(methacroylethoxy)phenyl] propane; 1,4 bis(methacroylmethyl) cyclohexane; and 2,2 bis(4'-methacroylphenyl) propane.

3. A composition according to claim 2, which further comprises a polymerization accelerator and a polymerization initiator.

4. A composition according to claim 3, wherein said polymerization accelerator is a tertiary aromatic amine and said polymerization initiator is benzoyl peroxide.

5. A composition according to claim 2, wherein said polymeric filler is a polyethylmethacrylate homopolymer.

6. A method for coating human nails comprising the steps of:
   (a) applying a curable liquid to human nails, said liquid comprising from about 21% to about 53% by weight of ethoxyethylmethacrylate, from about 0.2% to about 11% by weight of a cross-linking agent having at least two methacrylate groups per molecule, and from about 45% to about 71% by weight of a polymeric filler having at least 70% of ethylmethacrylate groups in a homopolymer or a copolymer with methyl methacrylate; and
   (b) curing said curable liquid applied to said nails within about 60 seconds to about 360 seconds.

7. A method according to claim 6 which, prior to said application step (a), further comprises the step of dissolving a powdery composition in a liquid composition, wherein:
   (I) said powdery composition comprises said polymeric filler and a polymerization initiator;
   (II) said liquid composition comprises from about 75% to about 97% by weight of said ethoxyethylmethacrylate, from about 1% to about 20% by weight of said cross-linking agent, and a polymerization accelerator; and
   (III) the ratio of said liquid composition to said powdery composition ranges from about 1.2:1 to about 1:2.5.

8. A method according to claim 6, wherein said cross-linking agent is selected from the group consisting of ethylene-, diethylene-, triethylene- and polyethyleneglycol dimethacrylate; propylene-, dipropylene-, tripropylene- and polypropyleneglycol dimethacrylate; hexanediol dimethacrylate; trimethylolpropane trimethacrylate; 2,2 bis[4'(3"-methacroyl-2'-hydroxypropoxyphenyl] propane; 2,2 bis[4'(methacroylethoxy)phenyl] propane; 1,4 bis(methacroylmethyl) cyclohexane; and 2,2 bis(4'-methacroylphenyl) propane.

9. A method according to claim 7, wherein said polymerization accelerator is a tertiary aromatic amine and said polymerization initiator is benzoyl peroxide.

10. A method according to claim 8, wherein said polymeric filler is a polyethylmethacrylate homopolymer.

11. A two-package human nail coating product comprising:
(A) a liquid comprising from about 75% to about 97% by weight of ethoxyethylmethacrylate, and from about 1% to about 20% by weight of a cross-linking agent having at least two methacrylate groups per molecule; and
(B) a powder comprising a polymeric filler having at least 70% of ethylmethacrylate groups in a homopolymer or a copolymer, methyl methacrylate wherein said liquid (A) and said powder (B) are separately contained in said product.

12. A product according to claim 11, wherein said cross-linking agent is selected from the group consisting of ethylene-, diethylene-, triethylene- and polyethyleneglycol dimethacrylate; propylene-, dipropylene-, tripropylene-, and polypropyleneglycol dimethacrylate; hexanediol dimethacrylate; trimethylolpropane trimethacrylate; 2,2 bis[4'(3''-methacroyl-2'-hydroxypropoxy)phenyl] propane; 2,2 bis[4'(methacroylethoxy)phenyl] propane; 1,4 bis(methacroylmethyl) cyclohexane; and 2,2 bis (4'methacroylphenyl) propane.

13. A product according to claim 12, wherein said liquid (A) further comprises a polymerization accelerator and said powder (B) further comprises a polymerization initiator.

14. A product according to claim 13, wherein said polymerization accelerator is a tertiary aromatic amine and said polymerization initiator is benzoyl peroxide.

15. A product according to claim 12, wherein said polymeric filler is a polyethylmethacrylate homopolymer.

16. A human nail coating composition according to claim 2 consisting essentially of said components (i), (ii) and (iii).

17. A method according to claim 8 wherein the curable liquid consists essentially of said ethoxyethylmethacrylate, cross-linking agent having at least two methacrylate groups per molecule and said ethylmethacrylate homopolymer or copolymer with methylmethacrylate.

* * * * *